US009044376B2

(12) United States Patent
Sun

(10) Patent No.: US 9,044,376 B2
(45) Date of Patent: Jun. 2, 2015

(54) MOXA HOLDER SUPPORT AND CUSTOMIZED MOXIBUSTION DEVICE COMPRISING THE SAME

(76) Inventor: Jae Kwang Sun, Seoul (KR)

( * ) Notice: Subject to any disclaimer, the term of this patent is extended or adjusted under 35 U.S.C. 154(b) by 807 days.

(21) Appl. No.: 13/057,152

(22) PCT Filed: Apr. 17, 2009

(86) PCT No.: PCT/KR2009/002005
§ 371 (c)(1),
(2), (4) Date: Feb. 1, 2011

(87) PCT Pub. No.: WO2010/013883
PCT Pub. Date: Feb. 4, 2010

(65) Prior Publication Data

US 2011/0190713 A1 Aug. 4, 2011

(30) Foreign Application Priority Data

Aug. 1, 2008 (KR) ........................ 10-2008-0075754
Aug. 1, 2008 (KR) ........................ 10-2008-0075756

(51) Int. Cl.
*A61F 7/00* (2006.01)
*A61M 37/00* (2006.01)
*A61H 39/06* (2006.01)

(52) U.S. Cl.
CPC ...................................... *A61H 39/06* (2013.01)

(58) Field of Classification Search
CPC . A61M 35/00; A61M 36/006; A61M 35/003; A61K 8/0208; A61B 19/42; A61B 18/14; A61F 7/007; A61F 2007/0001
USPC ............. 604/23–24, 289, 290, 313, 540, 541, 604/291; 607/96–113
See application file for complete search history.

(56) References Cited

U.S. PATENT DOCUMENTS

| | | | | | |
|---|---|---|---|---|---|
| 1,831,669 | A | * | 11/1931 | Kono | 604/24 |
| 2,464,457 | A | * | 3/1949 | Madaio | 128/893 |
| 3,224,439 | A | * | 12/1965 | Blair, Jr. | 602/18 |
| 4,175,543 | A | * | 11/1979 | Suzuki et al. | 600/549 |
| 4,203,438 | A | * | 5/1980 | Shiu | 604/24 |

(Continued)

FOREIGN PATENT DOCUMENTS

| | | |
|---|---|---|
| CN | 2089438 U | 11/1991 |
| CN | 2090259 U | 12/1991 |

(Continued)

OTHER PUBLICATIONS

International Search Report for PCT/KR2009/002005 Mailed on Nov. 19, 2009.

*Primary Examiner* — Melanie Hand
*Assistant Examiner* — Ned T Heffner
(74) *Attorney, Agent, or Firm* — AKC Patents, LLC; Aliki K. Collins

(57) ABSTRACT

The prevention invention relates to a moxa holder support and a moxibustion device comprising the same, and more particularly, to a moxa holder support which provides comfort to a patient receiving moxibustion, and to a moxibustion device in which the temperature of part of a human body, to which moxibustion is applied, can be easily controlled according to the characteristics of the related organ of the human body. When receiving moxibustion using the moxa holder support according to the present invention, a patient can feel comfortable because part of the patient's skin to which moxibustion is applied comes into contact with the leather connected to the bottom of a main body of the moxa holder support and the texture of pig skin, cow skin or sheep skin used as the leather in the present invention is similar to that of human skin. In addition, the moxibustion device according to the present invention, in which a moxa holder having a different thickness or a different number of air holes is employed depending on part of a human body to be treated can facilitate the control of the temperature of the part to be treated according to the characteristics of the related organ of the human body.

12 Claims, 3 Drawing Sheets

(56) References Cited

U.S. PATENT DOCUMENTS

| | | | | |
|---|---|---|---|---|
| 4,222,122 | A * | 9/1980 | Toms | 2/9 |
| 6,013,042 | A * | 1/2000 | Sakai | 601/134 |
| 2005/0089453 | A1 * | 4/2005 | Huang | 422/125 |
| 2006/0253089 | A1 * | 11/2006 | Lin | 604/301 |

FOREIGN PATENT DOCUMENTS

| | | | |
|---|---|---|---|
| CN | 200966748 | Y | 10/2007 |
| JP | 11076364 | A * | 3/1999 |
| KR | 20-1983-0001216 | | 7/1983 |
| KR | 20-2000-0003303 | | 2/2000 |
| KR | 20-0190920 | | 8/2000 |
| KR | 10-2002-0014449 | | 2/2002 |
| KR | 10-2002-0026925 | | 4/2002 |
| KR | 10-2004-0079673 | | 9/2004 |
| KR | 1020050009973 | A | 1/2005 |
| KR | 10-2006-0007450 | | 1/2006 |
| KR | 20-2008-000641 | | 4/2008 |

* cited by examiner

MOXA HOLDER SUPPORT AND CUSTOMIZED MOXIBUSTION DEVICE COMPRISING THE SAME

RELATED APPLICATIONS

This application is a 371 application of International Application No. PCT/KR2009/002005, filed Apr. 17, 2009, which in turn claims priority from Korean Patent Application Nos. 10-2008-0075756, filed Aug. 1, 2008, and 10-2008-0075754, filed Aug. 1, 2008, each of which is incorporated herein by reference in its entirety.

TECHNICAL FIELD

The present invention relates to a moxa holder support and a customized moxibustion device with the same, and in particular to a moxa holder support which provides a patient receiving moxibustion with comfort, and a moxibustion device which can easily control its temperature depending on the characteristics of an organ of a human body to which moxibustion is applied.

BACKGROUND ART

Moxibustion represents a kind of Korean traditional medical treatments, in which a certain medicine material like mugwort is burnt at a punctuation point in order to create a thermal stimulation on a skin surface, which leads to a vital reaction over a living body for thereby achieving a prevention and treatment of diseases. The effects of moxibustion treatment are numerous and excellent, of which one effect on a human body lies in facilitating a good blood circulation and helps clogged energy and blood circulate well, while enhancing a cellular immunity and a body fluid immune function, increasing the numbers of white blood cells and red blood cells and the amount of blood pigment, promoting a circulation speed and gluttony function of white blood cells, giving positive effects to blood glucose contents, potassium and calcium in blood and blood coagulation time, facilitating stomach digestion exercise and secretion of digestive juice, increasing the mass of a human body and achieving a pain killing operation by affecting an endocrine system.

The moxibustion device for performing moxibustion which is well known to have an excellent therapy effect in Korean traditional medical field comprises a moxa holder partitioned into a burning chamber and a moxibustion chamber by a moxibustion material support part, and a moxa holder support. When burning moxibustion materials placed at a moxa holder support part, heat is generated in the burning chamber, and the heat generated in the burning chamber is transferred to the moxibustion chamber, and the heat of the moxibustion chamber is transferred to a moxibustion portion of a human body. At this time, the temperature of the moxa holder remains at about 70° C., so when the moxa holder comes into direct contact with a moxibustion skin of a patient, the patient might have burns. In order to prevent such burns, the lower surface of the moxa holder is fixed to the moxa holder support, so the lower surface of the moxa holder support comes into contact with a moxibustion skin of a patient. However, the moxa holder support is generally made of elastic silicone with heat resistance. When silicone comes into contact with the skin of a human body, the patient whose skin is sensitive or has allergy or atopic dermatitis might feel uneasiness or might have side effects.

A method is conventionally disclosed, which is characterized in that a paper is inserted between a lower surface of a moxa holder support and a moxibustion skin of a patient in order to avoid a direct contact between a lower surface of a moxa holder support and a moxibustion skin of a patient, and it is suggested that a plastic wrap be covered on a moxibustion portion of a patient. The position of a moxa holder support might change by a slight movement of a patient in a moxibustion therapy, which makes an accurate moxibustion treatment impossible. When a moxibustion patient moves a lot, the moxa holder might fall down for thereby causing burns to a patient or making a fire.

The moxibustion is performed at a stomach or a back portion of a human body. In the Korean traditional medical treatment, it has been told that the stomach or back portion is classified into an upper body portion, a middle body portion and a low body portion, each of which is directly related with a specific organ of a human body. Therefore, it is needed to control a moxibustion time and the temperature of heat transferred to a moxibustion portion depending on the characteristics of an organ of a human body related with a portion to which a moxibustion is applied.

DISCLOSURE OF INVENTION

Accordingly, it is an object of the present invention to provide a moxa holder which makes it possible for a patient, who has a sensitive skin, allergy or atopic dermatitis, to feel comfortable in the course of moxibustion treatment by providing a lower surface of a moxa holder support with a material which does not harm a human body. In addition, since the position of a moxa holder support does not change by a slight movement of a patient, a moxibustion can be performed at an accurate portion of a human body. Even when a patient moves a lot, a moxa holder does not fall down, which results in preventing burns and fire.

It is another object of the present invention to provide a method for manufacturing a moxa holder support which makes it possible to achieve the above functions.

It is further another object of the present invention to provide a moxibustion device which makes it possible to easily control the temperature of a moxibustion portion depending on the characteristics of an organ of a human body related with a moxibustion portion and to concurrently perform a moxibustion with respect to the multiple portions of a human body while accurately pointing the portions to receive moxibustion treatments. Even when a patient who receives moxibustion moves a little, the position of a moxa holder does not change while preventing the moxa holder from falling down.

To achieve the above objects, there is provided a moxa holder support which comprises a moxa holder support body; and a leather which is secured to a lower surface of the moxa holder support body, wherein the moxa holder support body includes a close contact part secured to a lower side of the moxa holder, and the leather is selected from the group consisting of a pig skin, a cow skin and a sheep skin, and a through hole is formed at a portion of the leather corresponding to a through hole of the moxa holder support body.

To achieve the above objects, there is provided a method for manufacturing a moxa holder support which comprises a step (a) in which one leather selected from the group consisting of a pig skin, a cow skin and a sheep skin is secured to a lower surface of a moxa holder support body which includes a close contact part secured to a lower side of a moxa holder; a step (b) in which a sewing thread is inserted into the leather and a close contact part of the moxa holder support body for thereby sewing the same; and a step (c) in which a through hole is formed at a portion of the leather corresponding to a through hole of the moxa holder support body.

To achieve the above objects, there is provided a moxibustion device which comprises a moxa holder support; and a moxa holder which is mounted on a close contact part of the moxa holder support and is secured thereto, wherein the number of the moxa holders is the same as the number of the close contact parts, and the moxa holder is divided into a burning chamber and a moxibustion chamber by means of a moxibustion material support part installed in the interior, with the upper and lower sides of the moxa holder being open, and the thicknesses of the moxa holders or the number of the air holes formed at a side surface of the moxa holder are different from one another so that the temperature of the moxibustion chamber can be adjusted depending of the moxibustion portions of a patient. The moxibustion device further comprises a moxibustion cover with a close contact secured to an upper side of a moxa holder. The color of a moxa holder might change depending on a moxibustion portion of a human body.

ADVANTAGEOUS EFFECTS

When a moxibustion therapy is performed by using a moxa holder support according to the present invention, the skin of a patient corresponding to a moxibustion portion comes into contact with a leather secured to a lower surface of a moxa holder support body. Since a pig skin, a cow skin or a sheep skin feels like a skin of a human body, the patient in a moxibustion therapy can feel comfortable. So, the present invention can be well applied to a patient who has a sensitive skin, allergy or atopic dermatitis. Since the pig skin, cow skin and sheep skin has an excellent close contact performance with respect to a human body, even when a patient in a moxibustion therapy moves a little, the position of the moxa holder support does not change, while not falling down. A plurality of close contact parts are formed at the moxa holder support body. With the above constructions, even when a moxibustion treatment is concurrently performed with respect to multiple portions, since the contact area between the skin and the moxibustion portion increases, which results in an excellent therapy effect. Since a plurality of close contact parts secured to the lower side of the moxa holder are formed at the portions of the moxa holder support corresponding to the position of the moxibustion portion, multiple portions of a human body can be treated with moxibustion by accurately pointing the position to be applied with a moxibustion.

When performing a moxibustion by using a moxibustion device according to the present invention, since the thickness of the moxa holder determined depending on the portion of moxibustion or the number of the air holes formed at a side of the moxa holder are different, it is possible to easily control the temperature of the moxibustion portion depending on the characteristics of an organ of a human body. In addition, since the colors of the moxa holders are different depending on the portions of moxibustion, it is possible to easily perform moxibustion by selecting a moxa holder which deems to be proper for the moxibustion portion without checking the thickness of the moxa holder and the number of the air holes formed at the side of the moxa holder. In addition, since the moxibustion device according to the present invention comprises a moxa holder cover which is mounted at an upper side of the moxa holder, any possibilities of burns or air pollutions can be basically prevented in the course of removing the moxibustion device after using the same.

BRIEF DESCRIPTION OF THE DRAWINGS

The present invention will become better understood with reference to the accompanying drawings which are given only by way of illustration and thus are not limitative of the present invention, wherein.

MODES FOR CARRYING OUT THE INVENTION

One aspect of the present invention lies in a moxa holder support and in particular lies in a moxa holder support which provides a patient having a moxibustion treatment with comfort.

The preferred embodiments of the present invention will be described with reference to the accompanying drawings.

Figure 1:
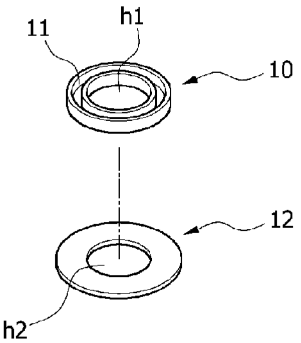
FIG. 1 is a disassembled perspective view illustrating a moxa holder support according to a first embodiment of the present invention.

FIG. 1 is a disassembled perspective view illustrating a moxa holder support according to a first embodiment of the present invention. The moxa holder support according to the present invention a moxa holder support body 10, and a leather 12 secured to a lower surface of the moxa holder support body. The moxa holder support body includes a close contact part 11 secured to a lower side of a moxa holder (now shown), which close contact part 11 is formed in a groove shape formed at a certain position of the moxa holder support body. A leather being larger or same as the lower surface of the moxa holder support body is secured to a lower surface of the moxa holder support body, which leather is formed of one material selected from the group consisting of a pig skin, a cow skin and a sheep skin. The moxa holder support body is equipped with a through hole h1 at an inner side of the close contact part, and a through hole h2 is formed at a portion of the leather corresponding to the through hole of the moxa holder support body. The size of the through hole formed at the leather is not limited thereto, but it is preferred that the size of the same is same or a little smaller than the size of the through hole of the moxa holder support body.

The moxa holder is mounted on the moxa holder support of the present invention and is secured thereto. Moxibustion material is inputted into the moxa holder and is burnt, after which moxibustion is performed. At this time, the skin of a patient who wants moxibustion therapy comes into contact with the leather secured to a lower surface of the moxa holder support body. Since a pig skin, a cow skin or a sheep skin is very similar with a skin of a human body, the patient who receives moxibustion therapy feels comfort. In particular, the pig skin is softer than other skins such as a cow skin or a sheep skin and has a very similar characteristic with the skin of a human body and is strong against heat, so it can be reliably used for the moxibustion therapy which is performed at a relatively higher temperature. Since the pig skin and the cow skin have excellent adherence to the skin of a human body, even when the patient moves a little, the position of the moxa holder support does not change, which leads to a reliable moxibustion at an accurate point, and even when the patient moves a lot, the moxa holder does not fall down for thereby preventing burns and fire.

The method for adhering one of a pig skin, a cow skin and a sheep skin to a lower surface of the moxa holder support body can be performed by using an adhesive or in a sewing way, which is not limited thereto. When using an adhesive, the component of the adhesive should be capable of bonding the material of the moxa holder support body and the selected skin. Since the adhesive might melt by means of heat in the course of moxibustion, it is preferred to sew by using a sewing thread. In particular, the moxa holder support body is made of a silicone material which has a strong heat resistance performance. When the material of the moxa holder support body is silicone, it is preferred that the leather is secured to a lower surface of the moxa holder support body with the aid of nylon thread which has a strong heat resistance.

In the moxa holder support according to the present invention, the number of the close contact parts of the moxa holder support body is not limited, but it is preferred that the number of the same is 2 through 9. In the moxa holder support according to the present invention, the position of the close contact part formed at the moxa holder support part is not limited, but it is preferred that the position of the moxa holder support body corresponding to the position of the moxibustion is proper.

Figure 2:
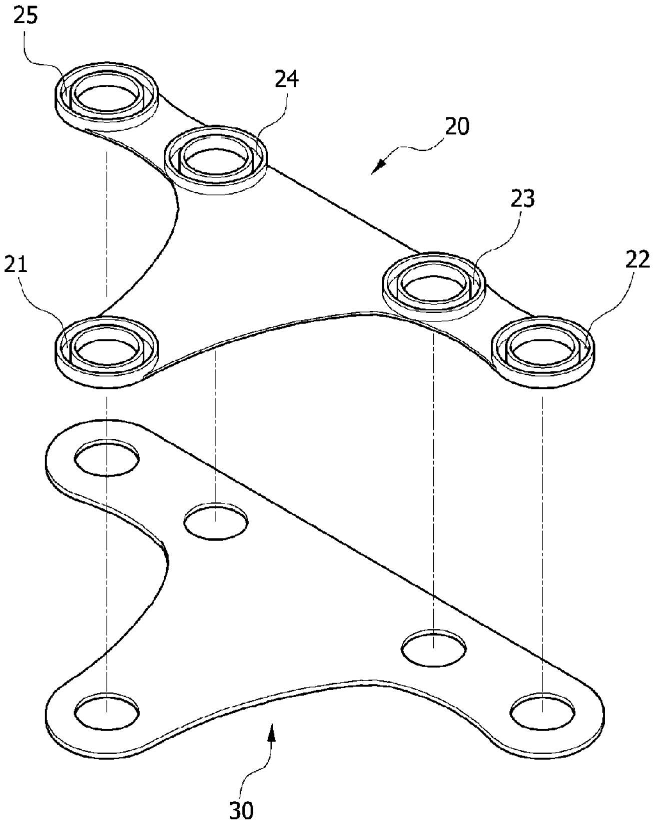
FIG. 2 is a disassembled perspective view illustrating a moxa holder support according to another embodiment of the present invention.

FIG. 2 is a disassembled perspective view illustrating a moxa holder support body according to another embodiment of the present invention. As shown in FIG. 2, five close contact parts 21, 22, 23, 24 and 25 are determined at the positions of the moxa holder support body 20 corresponding to the positions of the moxibustion when the moxibustion is Zhongwan(中脘), Tianshu(天樞), Daheng(大橫) which are specific portions in stomach. Zhongwan(中脘) is an acupuncture point belonging to Renmaie(任脈) according to Korean traditional medical field, at which a stomach is positioned, 12 centimeters above the navel. Tianshu(天樞) is an acupuncture point belonging to Yangming Stomach Meridian of Foot(足陽明胃經)) according to Korean traditional medical field, which is positioned at left and right sides of the navel and is generally used as a therapy point for large intestine diseases, diarrhea, etc. The Daheng(大橫) is an acupuncture point belonging to Taiyin Spleen Meridian of Foot (脾經) and is positioned at both sides of the navel, 12 centimeters away from the navel in left and right directions. The reference numeral 21 of FIG. 2 means a close contact part corresponding to Zhongwan(中脘) of Daheng(大橫), and the reference numerals 23 and 24 mean close contact parts corresponding to the position of Tianshu(天樞). The reference numerals 22 and 25 means close contact parts corresponding to the position of Daheng(大橫). As shown in FIG. 2, the moxa holder support according to the preset invention is characterized in that a plurality of close contact parts secured to the moxa holder are formed at the position of the moxibustion portions and the position of the moxa holder support body, by which it is possible to accurately point the positions of the moxibustion portions for thereby concurrently performing moxibustion therapy on multiple points. Since the contact area between the skin of the patient and the leather 30 secured to a lower surface of the moxa holder support body increases, it is possible to effectively prevent the position changes of the moxa holder support when a patient moves a little or the falling of the moxa holder due to the movement of the patient.

The number of the close contact parts limits the maximum number of the moxa holders which can be used concurrently. When the portions of moxibustion is divided into many detail parts, the number of the close contact parts increases, and the size and the close contact part and the size of the moxa holder become much smaller, but generally it is preferred that the maximum number of close contact parts is 9. A combination of the moxibustion portions and the number (or number of moxa holders) of the close contact parts are shown in Table 1.

TABLE 1

| Moxibustion portions | Number of close contact parts |
|---|---|
| Chest of front portion/upper portion of back | 2 |
| Upper, middle and lower portions of stomach/upper side of back/ Zhongwan(中脘) and Tianshu(天樞) | 3 |
| Upper and middle portions of stomach, middle and lower portions of stomach | 4 |
| Middle and lower portions of stomach/ Zhongwan(中脘), Tianshu(天樞) and Daheng(大橫) | 5 |
| Upper and middle portions of stomach/upper and middle portions of back/middle and lower portions of back | 6 |
| Upper, middle and lower portions of stomach/lower portion of back and waist | 7 |
| Upper, middle and lower portions of stomach/upper, middle and lower portions of back/back and whole waists | 8 or 9 |

FIG. 2 is a view illustrating the positions of the close contact parts and the number of the close contact parts when the moxibustion portions are Zhongwan(中脘), Tianshu(天樞) and Daheng(大橫) which are specific portions of the stomach. Table 1 shows the number of the close contact parts based on a combination of various moxibustion portions. However, the above disclosures are not limited thereto, namely, the position and number of the close contact parts might change in accordance with the combination of the specific portions of the stomach or the combination of the specific portions of the back.

Another aspect of the present invention lines in the method for manufacturing the moxa holder support according to the present invention.

The method for manufacturing the moxa holder support according to the present invention comprises a step (a) in which one leather selected from the group consisting of a pig skin, a cow skin and a sheep skin is secured to a lower surface of a moxa holder support body which includes a close contact part secured to a lower side of a moxa holder; a step (b) in which a sewing thread is inserted into the leather and a close contact part of the moxa holder support body for thereby sewing the same; and a step (c) in which a through hole is formed at a portion of the leather corresponding to a through hole of the moxa holder support body.

Here, the steps of the method for manufacturing the moxa holder support according to the present invention is generally (a), (b) and (c), but the sequence of (a), (c) and (b) is possible as well.

In the method for manufacturing the moxa holder support according to the present invention, the sewing thread used for combining the lower surface of the moxa holder support body and the leather might be any type of thread even when it has a strong heat resistance and a durable performance while not limiting thereto, but the thread is preferably nylon thread. The nylon thread fells soft and has a strong heat resistance and a high tensile strength and a high impact strength, so it can withstand with respect to the heat which occurs in the course of moxibustion. In particular, when the material of the moxa holder body is silicone, it is possible to easily secure a pig skin to a lower surface of the moxa holder support body.

Another aspect of the present invention lies in the moxibustion device, and in particular to the moxibustion device which can easily control the temperature of a moxibustion portion depending on the characteristics of an organ of a human body related to the moxibustion portion.

The moxibustion device according to the present invention comprises a moxa holder support and a moxa holder which is mounted on a close contact portion of the moxa holder support and is secured thereto. The number of the moxa holders to be mounted on the moxa holder support is determined depending on the number of the close contact parts formed at the moxa holder support body, and the number of the close contact parts is determined depending on the area of the moxibustion portions and the number of the moxibustion portions. When multiple portions are to be treated with moxibustions at one time, it is preferred that the number of the close contact parts is 2 to 9. At this time, the number of the moxa holders becomes same as the number of the close contact parts. The moxa holder is divided into a burning chamber and a moxibustion chamber by means of the moxibustion material support part installed in the interior, with the upper and lower sides of the moxibustion material support part being open. The thickness of the moxa holder or the number of the air holes formed at a side surface of the moxa holder are different so that the temperature of the moxibustion chamber can be controlled depending on the moxibustion portions.

Figure 3:
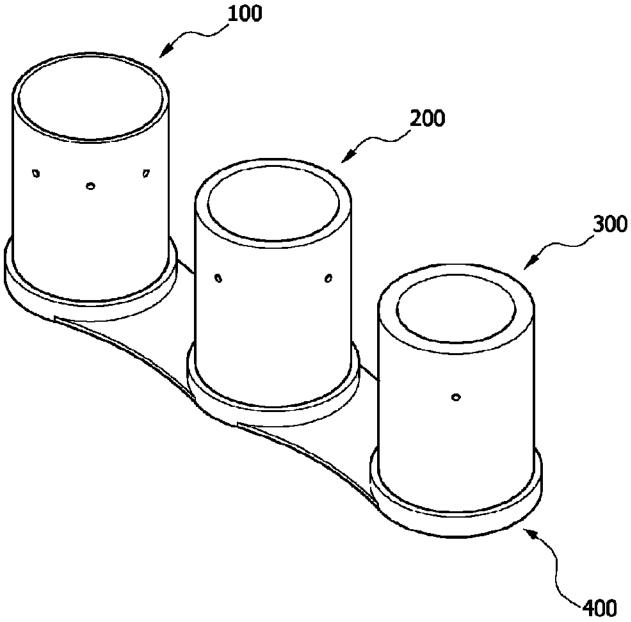
FIG. 3 is a schematic perspective view illustrating a moxibustion device according to an embodiment of the present invention.
Figure 4:
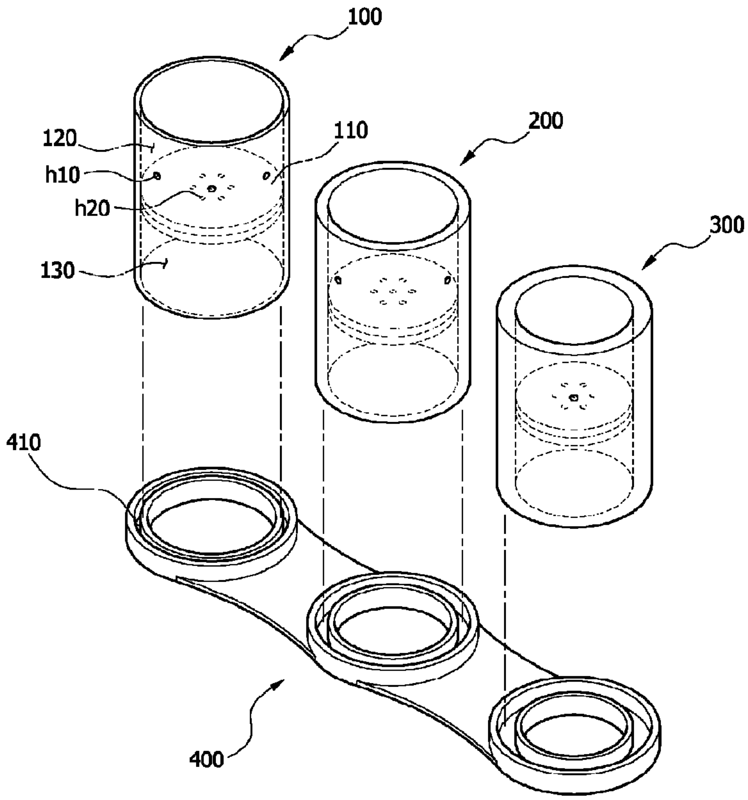
FIG. 4 is a disassembled perspective view illustrating a moxibustion device of FIG. 3.

FIG. 3 is a schematic perspective view illustrating a moxibustion device according to an embodiment of the present invention, and FIG. 4 is a disassembled perspective view illustrating a moxibustion device of FIG. 3. As shown in FIG. 3, the moxibustion device according to the present invention comprises moxa holders 100, 200 and 300, and a moxa holder support 400. As shown in FIG. 4, the moxa holder is divided into a burning chamber 120 and a moxibustion chamber 130 by means of a moxibustion material support part 110 installed in the interior, with the upper and lower sides of the moxibustion material support part being open. Air holes h10 each having a certain size are formed at a side surface of the moxa holder. A through hole h20 is formed at the moxibustion material support part 110 for effectively transferring the heat from the burning chamber to the moxibustion chamber. The moxa holder support part 400 is formed of a moxa holder support body and a leather secured to a lower surface of the moxa holder support body. The moxa holder support body includes a close contact part 410 secured to a lower side of the moxa holder. The close contact part is formed in a groove shape formed at a certain portion of the moxa holder support. As shown in FIG. 2, the groove is formed in a circular shape when the shape of the moxa holder is circular, but the shape of the same is not limited thereto. Namely, the shape might change in various forms depending on the shape of the moxa holder. A leather selected from the group consisting of a pig skin, a cow skin and a sheep skin is secured to a lower surface of the moxa holder support body having a close contact part.

Figure 5:
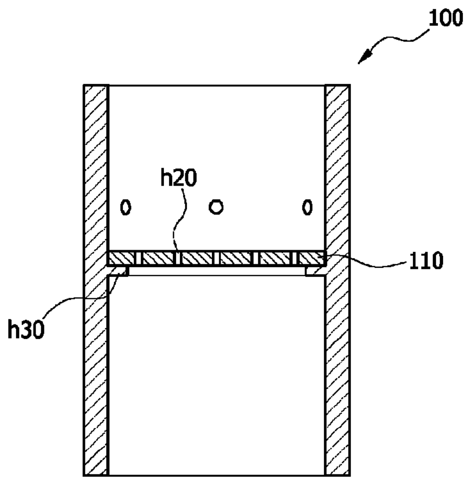
FIG. 5 is a cross sectional view illustrating an internal structure of a moxa holder applied to a moxibustion device according to an embodiment of the present invention.
Figure 6:
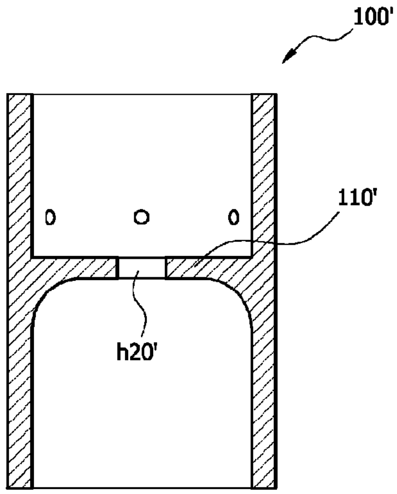
FIG. 6 is a vertical cross sectional view illustrating an internal structure of a moxa holder applied to a moxibustion device according to an embodiment of the present invention.

FIG. 5 is a cross sectional view illustrating an internal structure of a moxa holder applied to a moxibustion device according to an embodiment of the present invention, and FIG. 6 is a vertical cross sectional view illustrating an internal structure of a moxa holder applied to a moxibustion device according is to an embodiment of the present invention. As shown in FIG. 5, the moxibustion material support part 110 might be mounted on a protrusion h30 which is horizontally formed in the interior of the moxa holder 100, and the above disclosed construction is not limited thereto. In another example, the moxibustion material support part 110' of FIG. 6 might be made to be integral with the moxa holder when molding the moxa holder 100' at an initial manufacture stage. It is preferred that the through holes h20 and h20' are formed at the moxibustion material support parts 110 and 110' so as to effectively transfer the heat from the burning chamber to the moxibustion chamber. The above disclosed construction is not limited thereto. No through holes might be formed. The number of the through holes formed at the moxibustion material support part or the size of the through hole is not limited, but it is preferred that the size of the through hole is determined for the ash produced after the moxibustion material is burnt, to easily pass through the through hole. The moxibustion material support part is a part on which the moxibustion material is placed in the course of moxibustion. So, the heat generated when the moxibustion materials burns in the burning chamber can be transferred to the moxibustion chamber by means of conduction with the aid of the moxibustion material support part. When the through hole formed at the moxibustion material support part is clogged by means of the ash generating after the moxibustion material is burnt, it might be difficult to transfer the heat from the burning chamber to the moxibustion chamber.

The moxibustion is generally performed on a stomach portion or a back portion, and the stomach portion or back portion is divided into an upper body portion, a middle body portion and a lower body portion according to Korean traditional medical field. Each portion of the stomach or back is related with a certain organ of a human body. The upper body portion is related to a heart and a lung, and the middle body portion is related with a liver, a gall bladder, a spleen and a stomach, and the lower body portion is related to a kidney, a bladder, a small intestine and a large intestine. In case of the organ of a human body related to the portions of a stomach or a back, when a moxibustion is applied to an upper body portion such as a stomach or a back, the moxibustion time should be relatively shorter, and the temperature of the heat transferred from the interior of the moxibustion chamber of the moxa holder to the moxibustion portion should be relatively lower. When a moxibustion is applied to a middle body portion such as a stomach or a back, the moxibustion time and the temperature of the heat transferred from the interior of the moxibustion chamber of the moxa holder to the moxibustion portion should be in a middle range, and the when a moxibustion is applied to a lower body portion such as a stomach or a back, the moxibustion time is relatively longer and the temperature of the heat transferred from the interior of the moxibustion chamber of the moxa holder to the moxibustion portion should be relatively higher. When moxibustion is applied, the moxibustion time is generally controlled depending on the component, weight and shape of moxibustion material, but there is a limit for controlling the temperature of the heat transferred to the moxibustion portion by using only the moxibustion material.

The heat transfer method might be classified into conduction, convent ion and radiation. When applying a moxibustion by using the moxibustion device, the heat transfer between the burning chamber and external air, the moxibustion chamber and external air, the burning chamber and the moxibustion chamber, or the moxibustion chamber and the moxibustion portion is generally performed by conduction or convention. The convention takes place in the interior of a solid thing like heat continues to transfer from a high temperature to a low temperature without heat energy needing the movement of thing. When the heat transfer takes place by means of conduction, the thicker a solid thing is, which performs a heat transfer, the less the amount of heat is, which is transferred per hour. The convention is a phenomenon that heat energy is transferred from a high temperature to a low temperature along with the movements of material containing heat energy, namely, the movement of medium. When the heat transfer is performed by means of the convention, the more the movement of the medium is performed, which medium performs a heat transfer, the larger the amount of heat to be transferred is.

According to the moxibustion device according to an embodiment of the present invention, since the thickness of the moxa holder determined depending on the portion of the moxibustion or the number of the air holes of a side surface of the moxa holder are different from each other, the temperature of the moxibustion chamber can be easily controlled. Here, the thickness of the moxa holder corresponds to the thickness of the solid which performs a heat transfer when the heat transfer is performed by means of the conduction. The number of the air hole formed at a side surface of the moxa holder corresponds to a means for controlling the movement amount of the medium which performs a heat transfer when the heat transfer is performed by convention.

In more details, as the moxibustion portion more moves from the upper body portion such as a stomach or a back to the lower body portion, the temperature of the moxibustion chamber increases. The above temperature can be controlled by making the moxa holder used for the upper body portion such as a stomach or a back thinner while making the moxa holder used for the lower body portion such as a stomach or a back thicker. Here, it is characterized that the portion of which the thickness of the moxa holder is adjusted corresponds to the whole portions of the moxa holder, part of the moxa holder belonging to the burning chamber or part of the moxa holder belonging to the moxa holder. In addition, the number of the air holes formed at a side surface of the moxa holder used for the upper body portion such as a stomach or a back is relatively increased, and the number of the air holes formed at a side surface of the moxa holder used for the lower body portion such as a stomach or a back is relatively decreased. The portion where the air holes are formed is the whole surfaces of the moxa holder, a side surface of the moxa holder belonging to the burning chamber or a side surface of the moxa holder belonging to the moxa holder. The thickness of the moxa holder used for the middle body portion such as a stomach or a back or the number of the air holes formed at a side surface of the moxa holder have an intermediate thickness value between the upper body portion such as a stomach or a back and the lower body portion such as a stomach or a back and the number of the air holes formed at a side surface of the moxibustion chamber of the moxa holder. The thickness of the moxa holder based on the moxibustion portion and the number of the air holes of a side surface of the moxa holder might have various values depending on the components, weight, shape and others of the moxibustion material used, and when the compo components and moxibustion conditions of the moxibustion device are same except for the moxa holder, the above value has a certain interrelationship depending on the moxibustion portion.

The features of the moxa holder when moxibustion is applied to a back or a stomach under the normal conditions will be described when using the moxibustion device of FIG. 3 or 4.

It is characterized in that the moxa holder 100 placed on an upper side of a back or a stomach of a patient has 2.1~5.5 mm long thick and six air holes at a side surface of the same. It is preferred that the moxa holder has 3.0~4.0 mm long thick. The portion where the thickness of the moxa is controlled is the whole parts of the moxa holder, part of the moxa holder belonging to the burning chamber or part of the moxa holder belonging to the moxibustion chamber. The portion where the air holes are formed corresponds to the whole side surfaces of the moxa holder, a side surfaced of the moxa holder belonging to the burning chamber or a side surface of the moxa holder belonging to the moxibustion chamber. When the thickness of the moxa holder is less than 2.1 mm, since a lot of heat might be lost from the burning chamber or the moxibustion chamber to the outside of the moxa holder due to the convention, it is impossible to obtain a desired degree of temperature. When the thickness of the moxa holder exceeds 5.5 mm, the heat which might lose from the burning chamber or the moxa holder to the outside of the moxa holder due to the convention is too small, a proper temperature range with respect to the heart or lungs related to the upper body portion such as a stomach or a back might be exceeded. When the thickness of the moxa holder is 3.0~4.0 mm, it is possible to maintain the temperature of the lower side of the moxibustion chamber at 67~69° C. as the optimum temperature range with respect to the heart and lungs related with the upper body portion of the stomach or back, with the moxibustion chamber contacting with the moxibustion portion. In addition, when the number of the air holes formed at a side surface of the moxa holder is 6, a proper amount of heat loses from the burning chamber or the moxibustion chamber to the outside of the moxa holder by means of the convention, so it is possible to maintain an optimum temperature range with respect to the heart and lungs related with the upper body portion such as a stomach or a back.

It is characterized in that the moxa holder 200 placed at a middle portion such as a back or a stomach of a patient is 5.6~9.0 mm long thick, and the number of the air holes formed at a side surface of the moxa holder is 6. It is preferred that the thickness of the moxa holder is 6.5~7.5 mm. It is characterized in that the portion where the thickness of the moxa holder is adjusted is the whole portions of the moxa holder, part of the moxa holder belonging to the burning chamber or part of the moxa holder belonging to the moxibustion chamber, and it is characterized in that the portion where the air holes are formed is the whole portions of the moxa holder, a side surface of the moxa holder belonging to the burning chamber or a side surface of the moxa holder belonging to the moxibustion chamber. When the thickness of the moxa holder is less than 5.6 mm, a lot of the heat might be lost from the burning chamber or the moxibustion chamber to the outside of the moxa holder by means of the convention, and when the thickness of the moxa holder exceeds 9.0 mm, the heat losses from the burning chamber or the moxibustion chamber to the outside of the moxa holder due to the convention is too small, so it is impossible to maintain a proper temperature range with respect to a liver, a gall bladder, a spleen and a stomach which are relates to the upper body portion such as a stomach or a back. When the thickness of the moxa holder is 6.5~7.5 mm, the above temperature range is an optimum temperature range with respect to a liver, a gall bladder, a spleen and a stomach related to the middle body portion such as a stomach or a back, so it is possible to maintain the temperature of the lower side of the moxibustion chamber at 70~72° C., with the lower side of the moxa holder contacting with the moxibustion portion. When the number of the air holes formed at a side surface of the moxa holder is 5, a proper amount of heat losses from the burning chamber or the moxibustion chamber to the outside of the moxa holder due to convention, so it is possible to maintain an optimum temperature range with respect to a liver, a gall bladder, a spleen and a stomach related to the upper body portion such as a stomach or a back.

It is characterized in that the moxa holder 300 placed at a lower portion such as a back or a stomach of a patient is 9.1~12.5 mm long thick, and the number of the air holes formed at a side surface of the moxa holder is 4. It is preferred that the thickness of the moxa holder is 10.0~11.0 mm. It is characterized in that the portion where the thickness of the moxa holder is adjusted is the whole portions of the moxa holder, part of the moxa holder belonging to the burning chamber or part of the moxa holder belonging to the moxibustion chamber, and it is characterized in that the portion where the air holes are formed is the whole portions of the moxa holder, a side surface of the moxa holder belonging to the burning chamber or a side surface of the moxa holder belonging to the moxibustion chamber. When the thickness of the moxa holder is less than 9.1 mm, a lot of the heat might lose from the burning chamber or the moxibustion chamber to the outside of the moxa holder by means of the convention, and when the thickness of the moxa holder exceeds 12.5 mm, the heat that loses from the burning chamber or the moxibustion chamber to the outside of the moxa holder due to the convention is too small, so it is impossible to maintain a proper temperature range with respect to a kidney, a bladder, a small intestine and a large intestine which are relates to the lower body portion such as a stomach or a back. When the thickness of the moxa holder is 10.0~11.0 mm, the above temperature range is an optimum temperature range with respect to a kidney, a bladder, a small intestine and a large intestine related to the lower body portion such as a stomach or a back, so it is possible to maintain the temperature of the lower side of the moxibustion chamber at 73~75° C., with the lower side of the moxa holder contacting with the moxibustion portion. When the number of the air holes formed at a side surface of the moxa holder is 4, a proper amount of heat loses from the burning chamber or the moxibustion chamber to the outside of the moxa holder due to convention, so it is possible to maintain an optimum temperature range with respect to a kidney, a bladder, a small intestine and a large intestine related to the lower body portion such as a stomach or a back.

The features of the moxa holder have been described with respect to each element when a moxibustion is applied on an upper body portion, a middle body portion and a lower body portion such as a stomach or a back by using the moxibustion device of FIG. 3 or FIG. 4 for easier understanding, but since the area of the back is larger than the area of the stomach, the sizes or the numbers of the moxa holder, the moxa holder support and the close contact parts used for the same portions of the back should be larger or more than when applying the moxibustion device to the stomach. For example, when applying moxibustion on the upper, middle and lower body portions at one time, three moxa holders are needed, but four to nine moxa holders are actually needed with respect to the moxa holder having the same size as the moxa holder used on the stomach in order to apply moxibustion to the same portions of a back, provided that the above example might change in various forms depending on the shape of the patient who receives a moxibustion therapy.

It is preferred that the moxibustion device according to the present invention has the moxa holders of the different colors, which will be used for different portions depending on the positions of moxibustion. For example, when the upper, middle and lower body portions of the back or stomach receive a moxibustion by using the moxibustion device of FIGS. 3 and 4, it is possible to recognize the kinds of the moxa holders with different colors, of which the surface of the moxa holder 100 used for the upper body portion has a black color, the surface of the moxa holder 200 used for the middle body portion has a blue color, and the surface of the moxa holder 300 used for the lower body portion has a red color. A pigment might be added to the materials used for manufacturing the moxa holder for thereby making the colors of the moxa holders different from one another. The moxibustion device according to a preferred embodiment of the present invention has the different colors of the moxa holders depending on the moxibustion portions, it is possible to directly apply a moxibustion therapy by selecting a moxa holder proper to the moxibustion portion without checking the thickness of the moxa holder or the number of the air holes at a side surface of the moxibustion chamber. The operations that the moxibustion portions are an upper body portion, a middle body portion and a lower body portion of a back or a stomach, and the number of the moxa holders is 3 has been described, but the present invention is not limited thereto. The present invention might be changed depending on the numbers of moxibustion portions and moxa holders.

Figure 7:
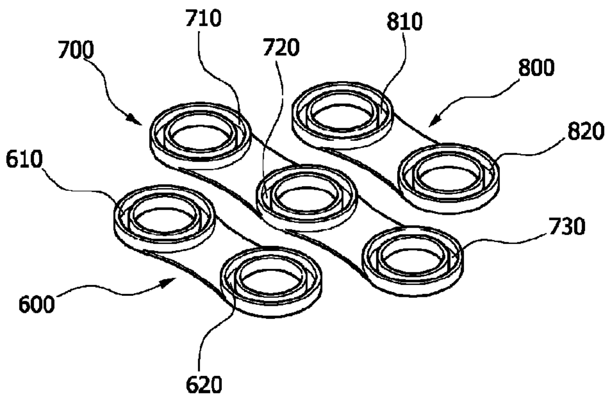
FIG. 7 is a perspective view illustrating a plurality of moxa holder supports applied to a moxibustion device according to another embodiment of the present invention.

In the descriptions of FIG. 3 or FIG. 4, the operations that multiple portions receive moxibustion by using one moxa holder support having three close contact parts, but the present invention is not limited thereto, namely, a combination of a plurality of moxa holders each having a plurality of close contact parts might be used. A combination of one or more moxa holder supports each having one close contact part and a plurality of moxa holder supports having a plurality of close contact parts might be used. FIG. 7 is a perspective view illustrating a plurality of moxa holders supports adapted to a moxibustion device according to another embodiment of the present invention. The plurality of the moxa holder supports of FIG. 7 might be used when performing a moxibustion therapy with respect to the upper, middle and lower body portions of a stomach. The moxa holder support 700 used for the upper body portion includes two close contact parts 610 and 620, and the moxa holder support 700 used for the middle body portion includes three close contact parts 710, 720 and 730, and the moxa holder support 800 used for the middle body portion has two close contact parts 810 and 820.

In addition, the moxibustion device according to the present invention might further include a moxa holder cover in addition to the moxa holder support and the moxa holder. The moxa holder includes a close contact part for securing to an upper side of the moxa holder. The moxa holder has the same construction as the moxa holder support from which the leather is removed from the lower surface of the moxa holder support body. It is preferred that the number of the close contact parts of the moxa holder cover is 2 to 9, and the material of the same is silicone. Since the temperature of the moxa holder is generally above 60° C. after the moxibustion on a patient is finished, a lot of care is needed when removing the moxibustion device from the moxibustion portion. When not taking care of removing, a user or other might have burns. Since ash is generated after moxibustion material is burnt and remains in the interior of the moxibustion device. So, the ash might pollute surrounding air when it comes out of the moxa holder while the moxibustion device moves. Since the moxibustion device according to the present invention is equipped with a moxa holder cover which is mounted on an upper side of the moxa holder and is secured thereto, it is possible to decrease any possibilities of burning danger or air pollution while the moxibustion device is removed after the moxibustion therapy is finished.

INDUSTRIAL APPLICABILITY

The moxa holder support and a customized moxibustion device comprising the same might be applied so as to loosen fatigue and pains of a user by preventing a low temperature phenomenon in a body and a cooled body portion which is a problem to modern people while obtaining powerful energy. In addition, the present invention might be used for preventing the occurrence of cancer, hypertension and stroke and treating the same by increasing the temperature of a body of a patient.

The invention claimed is:

1. A moxa holder support, comprising:

a body having a first through-hole formed therein;

a planar leather portion disposed at a bottom surface of the body to be coupled thereto, the leather portion having a second through-hole formed therein, the second through-hole corresponding to the first through-hole; and a groove formed in the body to receive therein a moxa holder;

wherein a material of the body is silicone and the leather portion is attached onto the bottom surface of the body via sewing of nylon thread.

2. The support of claim 1, wherein each of the body and the groove has a circular circumference.

3. The support of claim 1, wherein the second through-hole is equal or smaller than the first through-hole in a size.

4. A moxibustion device, comprising:

the moxa holder support according to claim 1;

a moxa holder inserted into the groove of the body; and a moxa holder cover comprising silicone.

5. The device of claim 4, wherein the holder is defined into a burning chamber and a moxibustion chamber via a moxibustion material support.

6. The device of claim 4, wherein a thickness of the holder or the number of air holes formed at a side surface of the holder depends on a temperature of the moxibustion chamber.

7. The device of claim 6, wherein the thickness is 2.1~5.5 mm or the number of the air holes is 6.

8. The device of claim 6, wherein the thickness is 5.6~9.0 mm or the number of the air holes is 5.

9. The device of claim 6, wherein the thickness is 9.1~12.5 mm or the number of the air holes is 4.

10. A method for manufacturing a moxa holder support, the method comprising:

providing a body having a first through-hole and a groove formed therein;

bringing a leather portion into contact with a bottom surface of the body;

combining the leather portion and the body via sewing of thread; and forming a second through-hole in the leather portion so as to correspond to the first through-hole.

11. The method of claim 10, wherein a material of the body is silicone, and the thread is nylon thread.

12. A moxa holder support, comprising:

a plurality of bodies, each having a first through-hole and a groove formed therein, the groove being configured to receive therein a moxa holder; and a planar leather portion disposed at all of bottom surfaces of the bodies so as to be coupled thereto, wherein the leather portion has a plurality of second through-holes formed therein, the second through-holes being spaced from each other, wherein the plurality of the second through-holes corresponds to the plurality of the first through-holes respectively.

* * * * *